US007316644B2

(12) United States Patent
Bray

(10) Patent No.: US 7,316,644 B2
(45) Date of Patent: Jan. 8, 2008

(54) METHOD FOR PREPARING PARTICLES OF RADIOACTIVE POWDER CONTAINING CESIUM-131 FOR USE IN BRACHYTHERAPY SOURCES

(75) Inventor: Lane Allan Bray, Richland, WA (US)

(73) Assignee: IsoRay Medical, Inc., Richland, WA (US)

( * ) Notice: Subject to any disclaimer, the term of this patent is extended or adjusted under 35 U.S.C. 154(b) by 0 days.

(21) Appl. No.: 11/198,873

(22) Filed: Aug. 5, 2005

(65) Prior Publication Data

US 2006/0167332 A1    Jul. 27, 2006

Related U.S. Application Data

(60) Provisional application No. 60/626,123, filed on Nov. 9, 2004, provisional application No. 60/602,392, filed on Aug. 18, 2004.

(51) Int. Cl.
*A61M 36/00*    (2006.01)
(52) U.S. Cl. .......................................................... 600/8
(58) Field of Classification Search ................. 600/1–8
See application file for complete search history.

(56) References Cited

U.S. PATENT DOCUMENTS

| | | | |
|---|---|---|---|
| 1,753,287 A | 4/1930 | Failla | |
| 3,351,049 A | 11/1967 | Lawrence | 128/1.2 |
| 3,706,689 A | 12/1972 | Haskins | 252/301.1 R |
| 4,323,055 A | 4/1982 | Kubiatowicz | 128/1.2 |
| 4,702,228 A | 10/1987 | Russell, Jr. et al. | 128/1.2 |
| 4,784,116 A | 11/1988 | Russell, Jr. et al. | 128/1.2 |
| 4,891,165 A | 1/1990 | Suthanthiran | 252/633 |
| 4,994,013 A | 2/1991 | Suthanthiran et al. | 600/8 |
| 5,071,610 A | 12/1991 | Hagan et al. | 264/120 |
| 5,163,896 A | 11/1992 | Suthanthiran et al. | 600/8 |
| 5,342,283 A | 8/1994 | Good | 600/8 |
| 5,368,736 A | 11/1994 | Horwitz et al. | 210/635 |
| 5,405,309 A | 4/1995 | Carden, Jr. | 600/3 |
| 5,512,256 A | 4/1996 | Bray et al. | 423/2 |
| 5,591,420 A * | 1/1997 | Balmer | 423/700 |
| 5,683,345 A | 11/1997 | Waksman et al. | 600/3 |
| 5,749,042 A | 5/1998 | Bray et al. | 423/2 |
| 5,899,882 A | 5/1999 | Waksman et al. | 604/96 |
| 6,060,036 A | 5/2000 | Armini | 424/1.29 |
| 6,066,302 A | 5/2000 | Bray | 423/2 |
| 6,099,457 A | 8/2000 | Good | 600/8 |
| 6,099,458 A | 8/2000 | Robertson | 600/8 |
| 6,139,749 A | 10/2000 | Goken et al. | 210/651 |
| 6,306,074 B1 | 10/2001 | Waksman et al. | 600/7 |
| 6,309,614 B1 | 10/2001 | Horwitz et al. | 423/2 |
| 6,351,049 B1 | 2/2002 | Chassoulier et al. | 310/90.5 |
| 6,403,916 B1 | 6/2002 | Spooner et al. | 219/121.63 |
| 6,458,070 B1 | 10/2002 | Waksman et al. | 600/3 |
| 6,471,632 B1 | 10/2002 | Jahrmarkt et al. | 600/8 |
| 6,479,920 B1 | 11/2002 | Lal et al. | 310/309 |
| 6,485,406 B1 | 11/2002 | Ziegler et al. | 600/8 |
| 6,503,185 B1 | 1/2003 | Waksman et al. | 600/3 |
| 6,554,756 B1 | 4/2003 | Schaart | 600/3 |
| 6,589,502 B1 | 7/2003 | Coniglione et al. | 424/1.25 |
| 6,608,277 B2 | 8/2003 | Spooner et al. | 219/121.63 |
| 6,666,811 B1 | 12/2003 | Good | 600/8 |
| 6,679,824 B1 * | 1/2004 | Reed et al. | 600/7 |
| 6,689,043 B1 | 2/2004 | McIntire et al. | 600/1 |
| 6,730,013 B1 * | 5/2004 | Shank et al. | 600/7 |
| 6,749,554 B1 | 6/2004 | Snow et al. | 600/3 |
| 6,821,242 B1 | 11/2004 | Waksman et al. | 600/3 |
| 2002/0022781 A1 | 2/2002 | McIntire et al. | 600/458 |
| 2002/0162828 A1 | 11/2002 | Spooner et al. | 219/121.63 |
| 2003/0088146 A1 | 5/2003 | Slater et al. | 600/8 |
| 2003/0092959 A1 | 5/2003 | Slater et al. | 600/8 |
| 2003/0229259 A1 | 12/2003 | Waksman et al. | 600/3 |
| 2004/0076579 A1 | 4/2004 | Coniglione et al. | 424/1.11 |
| 2004/0097779 A1 | 5/2004 | McIntire et al. | 600/1 |
| 2004/0192999 A1 | 9/2004 | Waksman et al. | 600/4 |
| 2004/0236169 A1 | 11/2004 | Slater et al. | 600/8 |
| 2004/0242953 A1 | 12/2004 | Good | 600/7 |
| 2006/0018813 A1 | 1/2006 | Bray | 423/11 |
| 2006/0024223 A1 | 2/2006 | Bray et al. | 423/1 |
| 2006/0051269 A1 | 3/2006 | Bray et al. | 423/158 |

FOREIGN PATENT DOCUMENTS

| | | |
|---|---|---|
| JP | 01-254900 | 10/1989 |
| WO | WO 00/51136 | 8/2000 |

(Continued)

OTHER PUBLICATIONS

3M Empore™ Rad Disks Product Listing, 1998. Available at http://www.mmm.com/empore, downloaded Mar. 11, 2004.
Balmer, M.L. et al., "New Silicotitanate Waste Forms: Development and Characterization," Interfacial and Processing Sciences Annual Report 1999. Available at http://www.pni.gov/microcats/aboutus/publications/microsystems/annual _report1999. Downloaded Sep. 19, 2004.
Hobbs, D.T., "Strategic Design and Optimization of Inorganic Sorbents for Cesium, Strontium, and Actinides," Westinghouse Savannah River Company Report WSRC-RP-2002-00337. Available at http://www.osti.gov/bridge. Downloaded Oct. 5, 2005.
Cary, A., "PNNL gel may charge drug obstacles," *Tri-City Herald*, Mar. 30, 2001. Available at http://www.tri-cityherald.com. Downloaded Oct. 8, 2004.
Hodgman, C.D. (ed.), "*Handbook of Chemistry and Physics, 31st edition*," Chemical Rubber Publishing Co., Cleveland, OH, pp. 408-409, 1949.
Hodgman, C.D. (ed.), "*Handbook of Chemistry and Physics, 31st edition*," Chemical Rubber Publishing Co., Cleveland, OH, pages 524-525, 1949.

(Continued)

*Primary Examiner*—Charles A. Marmor, II
*Assistant Examiner*—Christine D. Hopkins
(74) *Attorney, Agent, or Firm*—Seed IP Law Group PLLC

(57) ABSTRACT

The present invention provides a method of preparing Cesium-131 (Cs-131) as a dispersed radioisotope. Uses of the dispersed Cs-131 prepared by the method include cancer research and treatment, such as for the use in brachytherapy. Cs-131 is particularly useful in the treatment of faster growing tumors.

12 Claims, No Drawings

FOREIGN PATENT DOCUMENTS

WO WO 01/80251 10/2001
WO WO 2004/053892 6/2004

OTHER PUBLICATIONS

Kraus and Nelson, "Anion Exchange Studies of the Fission Products," in *Proc. Int. Conf. Peaceful Uses of Atomic Energy*, vol. 7, Geneve, 1955, pp. 113-125.

Naumann, R.A. et al., "Preparation of Radioactive Targets for Charged-Particle Nuclear Spectroscopy at the CERN-ISOLDE Project," *Nuclear Instruments and Methods in Physics Research B26*: 59-64, 1987.

pSiVida Company, BioSilicon internet web pages. Available at http://www.psivida.com.au/text. Downloaded Nov. 3, 2004.

Smith, L.L. et al., "Application of Empore™ Strontium Rad Disks to the Analysis of Radiostrontium in Environmental Water Samples," *Radiochemica Acts 73*:165-170, 1996.

Willard and Goodspeed, "Separation of Strontium, Barium, and Lead from Calcium and Other Metals," *Industrial and Engineering Chemistry 8*(6):414-418, 1936.

Harper, P.V. et al., "Isotopes Decaying by Electron Capture: a New Modality in Brachytherapy," in *Proceedings of the International Conference on the Peaceful Uses of Atomic Energy*, Geneva Switzerland, 1958, pp. 417-422.

Kurath, D.E. et al., "Ion Exchange Removal of Cesium from Simulated and Actual Hanford Tanks 241-SY-101 and 241-SY-103," in *Proceedings of the International Topical Meeting on Nuclear and Hazardous Waste Management Spectrum '96*, Aug. 18-23, 1996, Seattle, Washington, American Nuclear Society, La Grange Park, IL, 1996, pp. 222-228.

Wike, J.S. et al., "Chemistry for Commercial Scale Production of Yttrium-90 for Medical Research," *International Journal of Radiation Applications and Instrumentation Part A*, 41(9): 861-865, 1990.

"Radiation protection—Sealed radioactive sources—Leakage test methods," International Standard ISO 9978, First Edition, Feb. 15, 1992.

"Radiation protection—Sealed radioactive sources—General requirements and classification," International Standard ISO 2919, Second Edition, Feb. 15, 1992.

R. Braun et al., "Crystalline Silicotitanates—Novel Commercial Cesium Ion Exchangers," UOP, pp. 1-12, pre-Nov. 2003.

Heintz, B.H. et al., "Comparison of I-125 sources used for permanent interstitial implants," *Med. Phys. 28*(4): 671-682, Apr. 2001.

Henschke, U.K. et al., "Cesium-131 Seeds for Permanent Implants," *Radiology 85*(6): 1117-1119, Dec. 1965.

Korb, L.J. et al., "Modern Brachytherapy for Localized Prostate Cancers: The Northwest Hospital (Seattle) Experience," *Review in Urology 3*(1): 51-60, Winter 2001.

Armpilia, C.I. et al., "The Determination of Radiobiologically Optimized Half-lives for Radionuclides Used in Permanent Brachytherapy Implants," *Int. J. Radiation Oncology Biol. Phys. 55*(2): 378-385, 2003.

Malinin, A.B. et al., "Production of $^{131}$Cs Without a Carrier and Estimation of the Cross Section of the Reaction. $^{131}$Cs (n,γ) $^{132}$Cs on Thermal Neutrons," *Soviet Radiochemistry 14*(6): 896-899, Nov.-Dec. 1972.

\* cited by examiner

METHOD FOR PREPARING PARTICLES OF RADIOACTIVE POWDER CONTAINING CESIUM-131 FOR USE IN BRACHYTHERAPY SOURCES

CROSS-REFERENCES TO RELATED APPLICATIONS

This application claims the benefit under 35 U.S.C. § 119(e) of U.S. Provisional Patent Application No. 60/602,392 filed Aug. 18, 2004 and U.S. Provisional Patent Application No. 60/626,123 filed Nov. 9, 2004, where these two provisional applications are incorporated herein by reference in their entirety.

BACKGROUND OF THE INVENTION

1. Field of the Invention

The present invention relates generally to a method of dispersing Cesium-131 (Cs-131), including preparing particles of radioactive powder containing Cs-131. Uses of the dispersed Cs-131 prepared by the method include cancer research and treatment, such as for use in brachytherapy implant seeds and other sources independent of method of fabrication.

2. Description of the Related Art

Radiation therapy (radiotherapy) refers to the treatment of diseases, including primarily the treatment of tumors such as cancer, with radiation. Radiotherapy is used to destroy malignant or unwanted tissue without causing excessive damage to the nearby healthy tissues.

Ionizing radiation can be used to selectively destroy cancerous cells contained within healthy tissue. Malignant cells are normally more sensitive to radiation than healthy cells. Therefore, by applying radiation of the correct amount over the ideal time period, it is possible to destroy all of the undesired cancer cells while saving or minimizing damage to the healthy tissue. For many decades, localized cancer has often been cured by the application of a carefully determined quantity of ionizing radiation during an appropriate period of time. Various methods have been developed for irradiating cancerous tissue while minimizing damage to the nearby healthy tissue. Such methods include the use of high-energy radiation beams from linear accelerators and other devices designed for use in external beam radiotherapy.

Another method of radiotherapy includes brachytherapy. Here, substances in the form of seeds, needles, wires or catheters are implanted permanently or temporarily directed into/near the cancerous tumor. Historically, radioactive materials used have included radon, radium and iridium-192. More recently, the radioactive isotopes Cs-131, iodine (I-125), and palladium (Pd-103) have been used. Examples are described in U.S. Pat. Nos. 3,351,049; 4,323,055; and 4,784,116.

During the last 30 years, numerous articles have been published on the use of I-125 and Pd-103 in treating slow growth prostate cancer. Despite the demonstrated success in certain regards of I-125 and Pd-103, there are certain disadvantages and limitations in their use. While the total dose can be controlled by the quantity and spacing of the seeds, the dose rate is set by the half-life of the radioisotope (60 days for I-125 and 17 days for Pd-103). For use in faster growing tumors, the radiation should be delivered to the cancerous cells at a faster, more uniform rate, while simultaneously preserving all of the advantages of using a soft x-ray emitting radioisotope. Such cancers are those found in the brain, lung, pancreas, prostate and other tissues.

Cesium-131 (Cs-131) is a radionuclide product that is ideally suited for use in brachytherapy (cancer treatment using interstitial implants, i.e., "radioactive seeds"). The short half-life of Cs-131 makes the seeds effective against faster growing tumors such as those found in the brain, lung, and other sites (e.g., for prostate cancer).

Cesium-131 is produced by radioactive decay from neutron irradiated naturally occurring Ba-130 (natural Ba comprises about 0.1% Ba-130) or from enriched barium containing additional Ba-130, which captures a neutron, becoming Ba-131. Ba-131 then decays with an 11.5-day half-life to cesium-131, which subsequently decays with a 9.7-day half-life to stable xenon-130.

Due to the need for dispersed Cs-131 and the deficiencies in the current approaches in the art, there is a need for improved methods. The present invention fulfills this need and further provides other related advantages.

BRIEF SUMMARY OF THE INVENTION

Briefly stated, the present invention discloses a method of preparing Cs-131 (e.g., purified Cs-131) as a dispersed radioisotope. For example, a variety of powdered silicates and crystalline silicotitanates (CSTs) are prepared and doped or reacted with a solution of Cs-131 to produce microparticles of radioactive powder. The particles containing Cs-131 may be further reacted by use of heat or other bonding agents to tightly hold the Cs-131 in the particle structure. In turn, these extremely small sized radioactive particles (ranging from 0.001 to about 20 microns) can be evenly dispersed in a variety of organic, polymeric and inorganic matrices to manufacture a wide variety of devices, including therapeutic brachytherapy devices.

The present invention in one embodiment provides a method for preparing particles of radioactive powder containing Cs-131. The method comprises the step of contacting Cs-131 with a material to produce microparticles of radioactive powder containing Cs-131, wherein the material comprises at least one member of zeolites, aluminosilicates, crystalline silicotitanates, silicates, silicotungstates and oxides of silica.

In another embodiment, the present invention provides a method for preparing a brachytherapy device. The method comprises the step of dispersing the radioactive particles (prepared by the above method) in an organic, polymeric or inorganic matrix.

In another embodiment, the present invention provides a method of treating a tumor susceptible to radiation from Cs-131. The method comprises the step of subjecting the tumor to the brachytherapy device (prepared by the above method).

In another embodiment, the present invention provides a brachytherapy device. The brachytherapy device comprises microparticles of radioactive powder containing Cs-131, wherein the microparticles comprise Cs-131 and at least one member of zeolites, aluminosilicates, crystalline silicotitanates, silicates, silicotungstates and oxides of silica. In yet another embodiment, the brachytherapy device can be used in a method of treating a tumor susceptible to radiation from Cs-131, comprising the step of subjecting the tumor to the device.

DETAILED DESCRIPTION OF THE INVENTION

As noted above, the present invention is directed to the use of materials to prepare a radioactive powder of Cs-131 for a wide range of uses, including for brachytherapy therapeutic medical devices. Each of the materials is unique in attracting Cs-131 out of solution to attach or to adhere to the solid crystalline structures. For example, a variety of powdered silicates and crystalline silicotitanates (CSTs) are prepared and doped or reacted with a solution of Cs-131 to produce microparticles of radioactive powder. The Cs-131 containing particles may be further reacted by use of heat or other bonding agents to tightly hold the Cs-131 in the particle structure. In turn, these extremely small sized radioactive particles (ranging from 0.001 to about 20 microns) can be evenly dispersed in a variety of organic, polymeric (e.g., U.S. Pat. No. 6,589,502) and inorganic matrices to manufacture a wide variety of therapeutic brachytherapy devices.

Examples of powdered materials include the general classes of zeolites, sodium aluminosilicates, crystalline silicotitanates, silicates (Na, K, Li), silicotungstates, and oxides of silica; and combinations thereof. The family of crystalline silicotitanates are formulated, for example, from titanium oxide, silicon oxide, sodium oxide and niobium pentoxide. Powdered materials may be prepared by one of skill in the art or purchased commercially (e.g., PQ Corporation, Berwyn, Pa.; Sigma-Aldrich, St. Louis, Mo.; Fisher Chemical, Fairlawn, N.J.).

Cs-131 may be purified by a wide variety of ways well known to one of ordinary skill in the art. For example, U.S. Pat. No. 6,066,302 provides a method for purifying Cs-131.

As described above, Cs-131 is useful for example for cancer research and treatment, such as radiotherapy (e.g., to treat malignancies). Where it is desired to implant a radioactive substance (e.g., Cs-131) into/near a tumor for therapy (brachytherapy), dispersed Cs-131 may be used as part of the fabrication of brachytherapy implant substance (e.g., seed). As used herein, the term "tumor" includes other areas of cancerous tissue. The use of dispersed Cs-131 in brachytherapy implant substances is not dependent on the method of fabrication of the substances. The method of the present invention provides dispersed Cs-131 for these and other uses.

The following Examples are offered by way of illustration and not by way of limitation.

EXAMPLES

Cs-131 Particles of Radioactive Powder

Two specific samples of materials were tested for use with radiochemical Cs-131 (½ life=~10 days). The first sample contained 0.18 microgram (μg) of Cs adsorbed on ~1.7 milligrams (mg) of sodium silicate/aluminum oxide ceramic. The second sample contained 0.18 μg of Cs adsorbed on ~1.36 mg of sodium silicate/aluminum oxide ceramic containing 0.34 mg crystalline silicotitanate (CST), 20 wt % CST.

Each sample was washed with 1 mL of water or 1 mL of eye wash solution. Eye wash solution (~0.9% NaCl) was used to represent human body fluid. The samples were contacted for 10 minutes, 0.5 hr, 4 hr, or 16 hrs.

Results

TABLE 1

Each ~1.7 mg sample contained ~0.18 μg Cs, and contacted with 1-mL Water:

| Time, | 0 wt % CST | | 20 wt % CST | |
|---|---|---|---|---|
| hr | Result | Cs Released, % | Result* | Cs Released, % |
| 10 min | <0.002 μg/mL | ~1.1 | <0.001 μg/mL | ~0 |
| 0.5 | 0.002 | 1.1 | <0.001 | ~0 |
| 4 | 0.0038 | 2.1 | <0.001 | ~0 |
| 16 | 0.0052 | 2.9 | <0.001 | ~0 |

TABLE 2

Each ~1.7 mg sample contained ~0.18 μg Cs, and contacted with 1-mL of Eye Wash Solution:

| Time, | 0 wt % CST | | 20 wt % CST | |
|---|---|---|---|---|
| hr | Result | Cs Released, % | Result* | Cs Released, % |
| 10 min | 0.037 μg/mL | 20.3 | <0.001 μg/mL | ~0 |
| 0.5 | 0.063 | 34.6 | <0.001 | ~0 |
| 4 | 0.11 | 60.4 | <0.0014 | ~0 |
| 16 | 0.15 | 82.4 | <0.0015 | ~0 |

*Detection Limit ~0.001 μg/mL

The above results show that cesium attached to Na silicate/Al oxide ceramic will be slowly desorbed using water, i.e., 2.9% in 16 hrs. However when CST was also present, no loss was found. When the results were repeated for simulated body fluid (i.e., eye wash solution), >82% of the Cs was released when the cesium was attached to Na silicate/Al oxide ceramic. However when CST was also present, no loss was found.

In addition, when the percent CST was varied in the mixture of Na silicate/Al oxide, the maximum amount of cesium that could be attached to ~1.7 mg of total material was 2 μg, 30 μg, and 54 μg, respectively for 0%, 11.1% and 20 wt % CST. This is significant since 100 millicuries of Cs-131 represents 1 microgram Cs. Therefore, ~1.7 mg of 20 wt % CST powder could contain >5 Curies of Cs-131. In addition, based on the above leaching results with water and eye wash solution, CST neat or a ceramic dilution of this material could be used in a variety of ways to be placed in the body as an injectable suspended solid, mixed with a bio compatible silica gel, polymeric gel, or other gels, made into microspheres; or placed, sprayed, or injected into areas of cancer growth, e.g., such as breast tumors. The radioactive species (Cs-131) when attached to the CST micro particles will be held in place and not leached out of the specified target location by body fluids before providing beneficial radiation to the cancer growth. Typical Cs-131 radioactive dose requirements will vary with application; e.g., 10 μCi may require <$10^{-7}$ mg of powder.

Cs in CST is stable when heated to a glass ceramic. Since Cs is a (+1) ion, it will be difficult to attach it to an organic linker and therefore the use of, for example, CST powdered ion exchanger provides the carrier for many novel and unique applications for cancer research.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention.

The invention claimed is:

1. A method for preparing particles of radioactive powder containing Cs-131, comprising the step of contacting Cs-131 with a material to produce microparticles of radioactive powder containing Cs-131, wherein the material comprises a crystalline silicotitanate and an aluminosilicate.

2. The method of claim 1 wherein the material consists of a crystalline silicotitanate and an aluminosilicate.

3. The method of claim 1 further comprising exposing the radioactive particles to a bonding agent, whereby the agent increases the retention of the Cs-131 by the particles.

4. The method of claim 3 wherein the bonding agent is heat.

5. A method for preparing a brachytherapy device, comprising the step of dispersing the radioactive particles prepared according to the method of any one of claims 1-4 in an organic, polymeric or inorganic matrix.

6. A brachytherapy device, comprising a device prepared according to the method of claim 5.

7. A method of treating a tumor susceptible to radiation from Cs-131, comprising the step of subjecting the tumor to the brachytherapy device of claim 6.

8. A brachytherapy device, comprising microparticles of radioactive powder containing Cs-131, wherein the microparticles comprise Cs-131 and a crystalline silicotitanate and an aluminosilicate.

9. The brachytherapy device of claim 8 wherein the microparticles consist of Cs-131, a crystalline silicotitanate and an aluminosilicate.

10. The brachytherapy device of claim 8 or 9 wherein the microparticles are dispersed in an organic, polymeric or inorganic matrix.

11. A method of treating a tumor susceptible to radiation from Cs-131, comprising the step of subjecting the tumor to the brachytherapy device of claim 8 or claim 9.

12. A method of treating a tumor susceptible to radiation from Cs-131, comprising the step of subjecting the tumor to the brachytherapy device of claim 10.

* * * * *